(12) United States Patent
Zhang

(10) Patent No.: US 6,590,081 B1
(45) Date of Patent: Jul. 8, 2003

(54) CRYSTALLINE TERIPARATIDE

(75) Inventor: Faming Zhang, Carmel, IN (US)

(73) Assignee: Eli Lilly and Company, Indianapolis, IA (US)

( * ) Notice: Subject to any disclaimer, the term of this patent is extended or adjusted under 35 U.S.C. 154(b) by 0 days.

(21) Appl. No.: 09/555,447

(22) PCT Filed: Dec. 8, 1998

(86) PCT No.: PCT/US98/26044

§ 371 (c)(1),
(2), (4) Date: May 31, 2000

(87) PCT Pub. No.: WO99/31137

PCT Pub. Date: Jun. 24, 1999

Related U.S. Application Data

(60) Provisional application No. 60/069,875, filed on Dec. 18, 1997.

(51) Int. Cl.$^7$ ............................................... A61K 38/29
(52) U.S. Cl. ...................... 530/399; 530/324; 530/412; 530/427; 514/12
(58) Field of Search ................................ 530/399, 324, 530/412, 427; 514/12

(56) References Cited

U.S. PATENT DOCUMENTS

| 5,400,741 A | 3/1995 | DeTitta et al. ............... 117/206 |
| 5,419,278 A | 5/1995 | Carter ......................... 117/206 |

FOREIGN PATENT DOCUMENTS

| EP | 0 225 050 A2 | 6/1987 |
| EP | 0 553 539 A1 | 8/1993 |
| EP | 0 748 817 A2 | 12/1996 |

OTHER PUBLICATIONS

Jin et al., J. Biol. Chem. 275, 27238, 2000.*

Kanaori, et al., "Comparative Study of Chicken and Human Parathyroid Hormone—(1–34)—Peptides in Solution with SDS", Eur. J. Biochem. 249, 878–885, 1997.

Pellegrini, et al., "Addressing the Tertiary Structure of Human Parathyroid Hormone—(1–34)", The Journal of Biological Chemistry, vol. 273, No. 17, Apr., 10420–10427, 1998.

Reeve et al., "Anabolic effect of human parathyroid hormone fragment on trabecular bone in involutional osteoporosis: a multicentre trial", Br. Med. J., 280(6228) :1340–1344, 1980.

Reeve et al., "Anabolic Effect of Low Doses of a Fragment of Human Parathyroid Hormone on the Skeleton in Postmenopausal Osteoporosis", The Lancet, 1:1035–1038, 1976.

Reeve et al., "Preliminary Trial of Low Doses of Human Parathyroid Hormone 1–34 Peptide in Treatment of Osteoporosis", Calcif. Tissue Res., 21:469–477, 1976.

Hodsman et al., "Biochemical responses to sequential human parathyroid hormone (1–38) and calcitonin in osteoporotic patients", Bone and Mineral, 9(2) :137–152, 1990.

Tsai et al., "Bone Responsiveness to Parathyroid Hormone in Normal and Osteoporotic Postmenopausal Women", J. Clin. Endocrinol Metab., 69(5) :1024–1027, 1989.

Isaac et al., "Absence of Effect of 1–34 h PTH on Plasma TSH, GH, FSH, LH, ACTH and Cortisol in Normal Man", Horm. Metab. Res., 12(9) :487–488, 1980.

Law et al., "Rapid Development of Renal Resistance to Low Doses of Synthetic Bovine Parathyroid Hormone Fragment 1–34", J. Clin. Invest., 72(3) :1106–1113, 1983.

Hulter et al., "Chronic Continuous PTH Infusion Results in Hypertension in Normal Subjects", J. Clin Hypertens, 2(4) :360–370, 1986.

Hodsman et al., "Bone densitometric and histomorphometric responses to sequential human parathyroid hormone (1–38) and salmon calcitonin in osteoporotic patients", 14(1) :67–83, 1991.

Martindale, The Extra Pharmacoepia, The Pharmaceutical Press, London, 29$^{th}$ Edition, 1989 p. 1338 (Copy not provided).

* cited by examiner

*Primary Examiner*—Christopher S. F. Low
*Assistant Examiner*—David Lukton
(74) *Attorney, Agent, or Firm*—Thomas D. Webster

(57) ABSTRACT

Pure, stable crystalline forms of parathyroid hormone, particularly teriparatide, are described as well as methods of preparation and purification.

6 Claims, 2 Drawing Sheets

SEQUENCE LISTING

<160> NUMBER OF SEQ ID NOS: 2

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
             20                  25                  30

Asn Phe Val Ala Leu Gly Ala Pro Leu Ala Pro Arg Asp Ala Gly Ser
         35                  40                  45

Gln Arg Pro Arg Lys Lys Glu Asp Asn Val Leu Val Glu Ser His Glu
     50                  55                  60

Lys Ser Leu Gly Glu Ala Asp Lys Ala Asn Val Asp Val Leu Thr Lys
 65                  70                  75                  80

Ala Lys Ser Gln

<210> SEQ ID NO 2
<211> LENGTH: 34
<212> TYPE: PRT
<213> ORGANISM: Homo sapiens

<400> SEQUENCE: 2

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
             20                  25                  30

Asn Phe

CRYSTALLINE TERIPARATIDE

This application is a 371 of PCT/US98/26044, filed Dec. 8, 1998, which claims priority from provisional application No. 60/069,875, filed Dec. 18, 1997.

TECHNICAL FIELD

This invention relates to a pure crystalline form of a parathyroid hormone. More particularly, the invention relates to the crystalline form of teriparatide, PTH(1–34), and methods of preparation and purification of the fragmented hormone.

BACKGROUND OF THE INVENTION

Parathyroid hormone (PTH) is a secreted, 84 amino acid product of the mammalian parathyroid gland that controls serum calcium levels through its action on various tissues, including bone. Studies in humans with certain forms of PTH have demonstrated an anabolic effect on bone, and have prompted significant interest in its use for the treatment of osteoporosis and related bone disorders.

Using the N-terminal 34 amino acids of the bovine and human hormone for example, which by all published accounts are deemed biologically equivalent to the full length hormone, it has been demonstrated in humans that parathyroid hormone enhances bone growth particularly when administered in pulsatile fashion by the sub-cutaneous and intravenous routes. A slightly different form of PTH, human PTH(1–38) has shown similar results.

PTH preparations have been reconstituted from fresh or lyophilized hormone, and incorporate various forms of carrier, excipient and vehicle. Most are prepared in water-based vehicles such as saline, or water acidified typically with acetic acid to solubilize the hormone. The majority of reported formulations also incorporate albumin as a stabilizer (see for example Reeve et al., Br. Med. J., 1980, 280:6228; Reeve at al., Lancet, 1976, 1:1035; Reeve at al., Calcif. Tissue Res., 1976, 21:469; Hodsman et al., Bone Miner; 1990, 9(2):137; Tsai et al., J. Clin. Endocrinol Metab., 1989, 69(5):1024; Isaac et al., Horm. Metab. Res., 1980, 12(9):487; Law et al., J. Clin Invest. 1983, 72(3):1106; and Hulter, J. Clin Hypertens, 1986, 2(4):360). Other reported formulations have incorporated an excipient such as mannitol, which is present either with the lyophilized hormone or in the reconstitution vehicle. Formulations representative of those employed for human studies include a human PTH(1–34) (SEQ ID NO: 2) preparation consisting, upon reconstitution, of mannitol, heat inactivated human serum albumin, and caproic acid (a protease inhibitor) as absorption enhancer (see Reeve at al., 1976, Calcif. Tissue Res., 21, Suppl., 469–477); a human PTH(1–38) preparation reconstituted into a saline vehicle (see Hodsman et al., 1991, 14(1), 67–83); and a bovine PTH(1–34) preparation in aqueous vehicle pH adjusted with acetic acid and containing albumin. There is also an International Reference preparation which for human PTH (1–84) (SEQ ID NO: 1) consists of 100 ng of hormone ampouled with 250 µg human serum albumin and 1.25 mg lactose (1981), and for bovine PTH (1–84) consists of 10 µg lyophilized hormone in 0.01 M acetic acid and 0.1% w/v mannitol (see Martindale, The Extra Pharmacoepia, The Pharmaceutical Press, London, 29th Edition, 1989 at p. 1338).

Commercial exploitation of parathyroid hormone requires the development of a formulation that is acceptable in terms of storage stability and ease of preparation. Because it is a protein and thus far more labile than the traditionally small molecular weight drugs, however, the formulation of parathyroid hormone presents challenges not commonly encountered by the pharmaceutical industry. Furthermore, like other proteins that have been formulated successfully, PTH is particularly sensitive to oxidation, deamidation and hydrolysis and further requires that its N-terminal and C-terminal sequences remain intact in order to preserve bioactivity.

SUMMARY OF THE INVENTION

The present invention provides methods of preparing crystalline forms of a fragmented parathyroid hormone (PTH) which heretofore have not been reported. The advantages of a crystalline form for the hormone are purity of the product and storage stability. Thus, for example, a crystalline form of PTH may be easily dissolved in a sterile solution in vials for parenteral administration. As a crystalline material, PTH may also be formulated, if desired, into other compositions such as, for example, tablets, capsules or suppositories.

Accordingly, in a first aspect the present invention is a novel crystalline form of a parathyroid hormone selected from the group consisting of PTH(1–34). PTH(1–37), PTH (1–38) and PTH(1–41), and, in particular crystalline human PTH(1–34) (SEQ ID NO: 2), generically known as teriparatide in the form of tetragonal plates or cubic crystals, both having a space group P422 and the following unit cell constants: a=b=91.071 Å, c=37.665 Å, $\alpha=\beta=\gamma=90°$.

A second aspect of the present invention is a process for purifying a parathyroid hormone including the steps of:
  (a) providing an aqueous solution of said hormone at a concentration of about 5 to 40 mg per ml;
  (b) mixing said solution with a reservoir solution comprising organic solvent at a concentration of about 5 to about 50 volume percent and a buffer at a concentration to maintain the pH between about 6.0 and about 12.0; and
  (c) allowing the resulting solution to stand at a predetermined time at a temperature between about room temperature and about 4° C. until plate-like crystals form.

A third aspect of the present invention is a process for purifying a parathyroid hormone where the steps include:
  (a) providing an aqueous solution of said hormone at a concentration of about 5 to 40 mg/ml;
  (b) mixing said solution with a reservoir solution comprising a phosphate or formate salt precipitant at the concentration of about 0.5M to 2.5M and, optionally, an aqueous buffer solution, or a mixture thereof, at a concentration to maintain a pH between about 4.0 and 6.0; and
  (c) allowing the resulting solution to stand at a predetermined time at a temperature between about room temperature and about 4° C. until cubic crystals form.

A fourth aspect of the present invention is a novel crystalline form of a parathyroid hormone selected from the group consisting of PTH(1–34), PTH(1–37), PTH(1–38), and PTH(1–41), and, in particular crystalline human PTH (1–34) (SEQ ID NO: 2) in the form of hexagonal crystals having a space group P622 and the following cell constants: a=b=30.169 Å, c=110.597 Å, $\alpha=\beta 90°$, $\gamma=120°$.

Finally, as a fifth aspect, the present invention is a process for purifying a parathyroid hormone comprising:
  (a) providing a solution of a parathyroid hormone selected from the group consisting of PTH(1–34), PTH(1–37), PTH(1–38), and PTH(1–41) at a concentration of about 5 to about 40 mg/ml in about 10 to about 30 volume percent glycerol;

(b) mixing said solution with a reservoir solution comprising organic solvent at a concentration of about 5 to about 50 volume percent, ammonium sulfate at a concentration of about 0.5M to 3.0M, and a buffer at a concentration to maintain the pH of the solution between about 3.0 and about 7.0; and (c) allowing the resulting solution to stand at a predetermined time at a temperature between about room temperature and about 4° C. until hexagonal crystals form.

DETAILED DESCRIPTION

Figure 1:
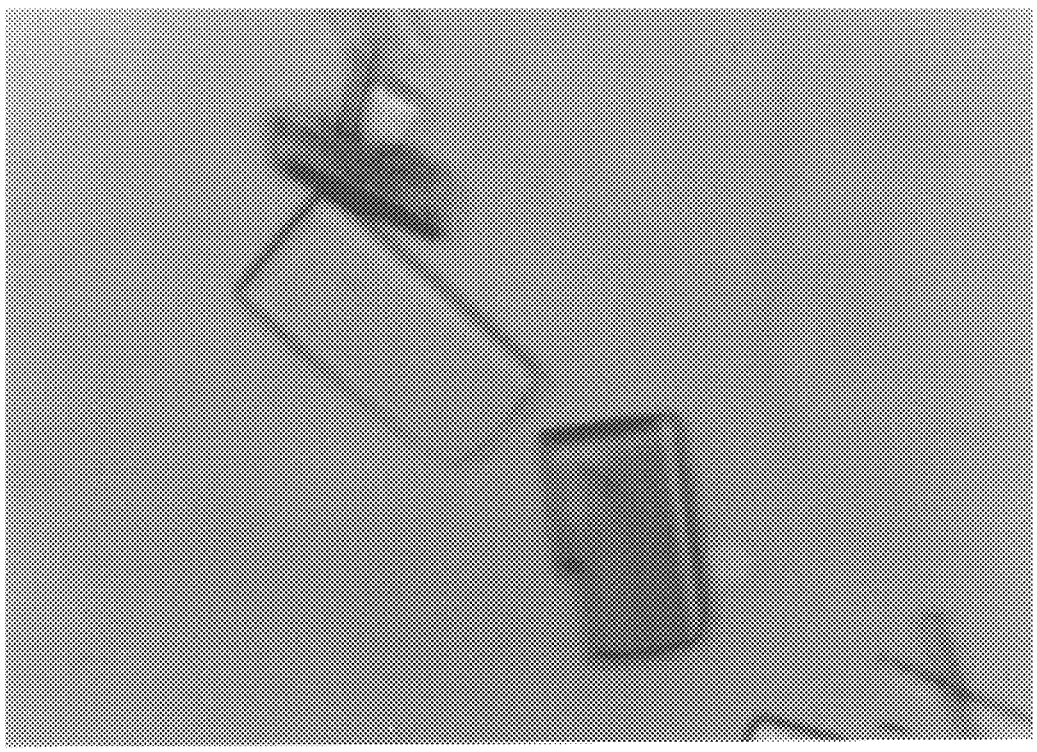
FIG. 1 is a photograph showing PTH(1–34) crystals grown from Example 1.

The invention relates to a pure crystalline form of a fragmented parathyroid hormone in its most stable form for storage and direct use in pharmaceutical compositions for administering to human patients.

The crystalline material may incorporate as active ingredient fragments or variants of fragments of human PTH or of rat, porcine or bovine PTH that have human PTH activity as determined in the ovarectomized rat model of osteoporosis reported by Kimmel et al., Endocrinology, 1993, 32(4):1577.

The parathyroid hormone fragments desirably incorporate at least the first 34 N-terminal residues, such as PTH(1–34), PTH(1–37), PTH(1–38) and PTH(1–41). Alternatives in the form of PTH variants incorporate from 1 to 5 amino acid substitutions that improve PTH stability and half-life, such as the replacement of methionine residues at positions 8 and/or 18 with leucine or other hydrophobic amino acid that improves PTH stability against oxidation and the replacement of amino acids in the 25–27 region with trypsin-insensitive amino acids such as histidine or other amino acid that improves PTH stability against protease. These forms of PTH are embraced by the term "parathyroid hormone" as used generically herein. The preferred hormone is human PTH(1–34) (SEQ ID NO: 2) also known as teriparatide. The hormones may be obtained by known recombinant or synthetic methods, such as described in U.S. Pat. No. 4,086,196, incorporated herein by reference.

PTH crystals embodying the invention may be prepared or grown from a reservoir or precipitant solution containing a buffer and, optionally, an organic solvent or salt, with the concentration of reagents and pH being carefully controlled within prescribed limits. Any of the well known basic crystallization techniques may be used for growth of the hormone crystals. Crystals may be grown, for example, at both room temperature and down to about 4° C., by using a sitting drop, hanging drop, seeding and/or batch crystallization apparatus. The batch method is obviously preferred for large scale preparations.

In the hanging drop method a small drop of protein solution is placed on a cover slip, or glass plate, which is inverted over a well of solution and sealed. The solution in the well contains a precipitating agent, which is also present in a lesser amount in the protein droplet. The function of the precipitating agent is twofold. First, the solution in the well is initially at a lower vapor pressure than the protein droplet so that evaporation progresses at a rate fixed by the difference in the vapor pressures and the distance by which the vapor (usually water) must diffuse. Secondly, the precipitating agent lowers the solubility of the protein in solution by competing with the protein for available solvent, and thus as evaporation from the protein droplet occurs the solution becomes supersaturated in protein. Under the appropriate conditions including pH, protein concentration and temperature, crystallization of the protein or macromolecule then occurs.

The batch methods generally involve the slow addition of a precipitating agent to an aqueous solution of protein until the solution just becomes turbid, at this point the container is sealed and left undisturbed for a predetermined time.

The PTH crystals may be obtained using either basic conditions or acidic conditions with any of the above methods.

Under basic conditions, the PTH fragment is first obtained in purified, lyophilized form. The lyophilized protein is dissolved in water at a concentration from about 5 mg/ml to about 40 mg/ml, preferably about 5 mg/ml to about 20 mg/ml. The aqueous protein solution is then mixed with a reservoir solution containing from about 5 to about 50 volume percent, preferably about 10 to 20 volume percent of an organic solvent and a buffer in an amount to maintain a pH range of about 6.0–12.0. The aqueous solution and the reservoir solution are preferably mixed in a 1:1 ratio.

The organic solvent used may be, for example and without limitation, methanol, ethanol, isopropanol, MPD, polyethylene glycol, ethylene glycol, or a mixture thereof. Any buffer may be used, preferably any biological buffer, e.g. the tris(hydroxymethyl)aminomethane salts, e.g. maleate or hydrochloride, or a glycine buffer. Alkali metal salts may also be used depending on the desired pH. For example, a citrate source such as sodium citrate may be used as a slightly basic buffer.

Crystallization in basic conditions affords plate-like crystals. Particularly, for example, teriparatide plate-like crystals have been grown using the above-described basic conditions within approximately 48 hours at room temperature and at 4° C. with an approximate size of 0.1 mm×0.1 mm×0.05 mm.

In acid conditions, the PTH fragment is prepared in the same manner in an aqueous solution at a concentration of about 5 mg/ml to about 40 mg/ml, preferably about 5mg/ml to about 20 mg/ml. The aqueous solution containing the protein is mixed with a reservoir solution containing a salt and/or buffer in an amount to maintain a pH between about 4.0 and about 6.0. The protein and buffer solutions are preferably mixed in a 1:1 ratio.

The reservoir solution contains a precipitant salt such as, for example, a phosphate formate at a concentration of about 0.5M to about 2.5M.

The buffer employed in the reservoir solution may be any biologically acceptable buffer at pH range 4.0–6.0. Such buffers are, for example various phosphates, formates, acetates, tartrates and the like including mixtures thereof, which are in the form of their respective alkali metal salts, e.g. sodium and/or potassium. When a phosphate or formate salt is used as the precipitant salt, an additional buffer may be added only if desired.

Crystallization in acidic media affords cube-like crystals. Thus, for example, teriparatide cube-like crystals have been grown within approximately 48 hours using the above described acidic conditions at room temperature and at 4° C. with an approximate size of 0 mm×0.1 mm×0.1 mm.

The preferred embodiment of the present invention is the crystalline form of teriparatide, human PTH(1–34) (SEQ ID NO: 2). Crystalline teriparatide prepared by the above-described methods has been characterized by x-ray crystallography as having a crystal system of tetragonal plates or cubic crystals with a symmetry or space group of P422 and the following cell dimension having unit cell constants:

a=b=91.071 Angstroms (Å), c=37.665Å,

α=β=γ=90°

Under an alternate embodiment, the PTH fragment obtained as described above is dissolved in a solution containing from about 10 to about 30 volume percent glycerol, preferably about 20 volume percent, where tie protein concentration is from about 5 mg to about 40 mg/ml, preferably about 5 mg/ml to about 2 mg/ml. The glycerol protein solution is then mixed with a reservoir solution containing from about 5 to about 50 volume percent, preferably about 5 to 20 volume percent of an organic solvent, and a buffer in an amount to maintain a pH range of about 3.0 to about 7.0. The protein solution and the reservoir solution are preferably mixed in a 1:1 ratio.

The organic solvents are those previously described. Isopropanol is preferred. Buffers previously described may also be used depending on the desired pH within the 3–7 range. Preferred as a buffer is a citrate salt, e.g. sodium citrate. In addition to the above solvent and buffer, the reservoir solution contains a precipitant salt such as ammonium sulfate at a concentration of about 0.5 to 3.0M.

Crystallization in the glycerol media affords hexagonal-like crystals. Thus, for example, human PTH(1–34) (SEQ ID NO: 2) hexagonal-like crystals have been grown within about 12–24 hours using the above-described conditions at room temperature and at 4° C. with an approximate size of 0.2 mm×0.2 mm×0.6 mm. X-ray crystallography of the hexagonal-like crystals show a crystal system with a symmetry or space group P622 and the following cell dimension having unit cell constants: a=b=30.169Å, c=110.597 Å, α=β=90°, γ=120°.

The advantages of a crystalline form for fragmented PTH and especially for teriparatide is that the crystalline material once obtained provides the active therapeutic ingredient in its most pure and stable form. Thus, the crystalline material may be stored with a longer shelf life than prior forms of the hormone or solutions thereof. The crystalline material may then be directly used to prepare pharmaceutical formulations for administration to patients. Thus, for example, the crystalline PTH may be dissolved directly with sterile solutions into vials or cartridges for parenteral administration.

The PTH solution incorporates PTH in a medically effective amount, a term used with reference to amounts useful either therapeutically or in medical diagnosis. The particular amount of parathyroid hormone incorporated in the preparation can be pre-determined based on the type of PTH selected and on the intended end-use of the preparation. In one application, the preparations are exploited for therapeutic purposes, and particularly for the treatment of osteoporosis. Osteoporosis therapy entails administration of the reconstituted preparation by injection, desirably subcutaneous injection, in unit doses that reflect the prescribed treatment regimen but are, by way of example, for human PTH(1–34) (SEQ ID NO: 2), within the range from 25 μg PTH/mL of injected solution to 1000 μg/mL of injected solution per patient, with injection volumes being desirably from 0.02 to 1.3 mL. Accordingly, crystalline hPTH(1–34) (SEQ ID NO: 2) is desirably incorporated with a buffering agent and excipient to form an aqueous solution containing PTH in a concentration range from 25 μg/mL to 1000 μ/mL, preferably 100 μ/mL to 500 μg/mL.

In one embodiment, the preparations are provided in a form that yields a unit container of 100–500 μg human PTH(1–34) (SEQ ID NO: 2) upon reconstitution into about 1 mL (0.8–1.2 mL) of the reconstitution vehicle, and the vials are accordingly loaded with about 1 mL of the aqueous PTH preparation, for subsequent freeze-drying.

Once the preparation is obtained as an aqueous solution containing desired amounts and concentrations of the buffering agent, excipient and PTH, individual vials are filled with the solution to the desired volume. The advantage of the present invention is that the above solution may be prepared with sterile water without the need to undergo a freeze-drying process.

In addition to their therapeutic use, the present PTH composition can be formulated and administered to aid in medical diagnosis and particularly to assist in establishing the diagnosis of hypoparathyroidism and pseudohypoparathyroidism in hypocalcemic patients. Except for the dose of PTH, the composition of the PTH preparation will remain as described herein for therapeutic use. An intravenously infused, single dose of human PTH(1–34) (SEQ ID NO: 2) that is equal to 200 International Units of PTH activity is appropriate for this diagnostic purpose. Diagnosis is then made by determining the effect of administered PTH or urinary cAMP levels, with cAMP elevation being indicative of the hypoparathyroidism condition, rather than its pseudo-form.

Since fragmented PTH is now available in a pure crystalline form, other dosage forms such as tablets, capsules, suppositories and the like may also be prepared for therapeutic or diagnostic administration.

The examples which follow are illustrative of the invention and are not intended to be limiting.

EXAMPLES

Example 1

Recombinant human rhPTH(1–34) (SEQ ID NO: 2) was prepared from material previously purified and lyophilized. The lyophilized protein was solubilized in water, at the concentration from 5 mg/ml to 20 mg/ml. The protein was mixed with reservoir solution (20% iso-propanol, 0.2M sodium citrate, 0.1M Tris.HCl buffer, pH=8.0) at 1:1 ratio on silicon coated glass cover slips. These cover slips were inverted and sealed over wells containing 1 ml of reservoir solution. Crystals appeared as tetragonal plates within 48–96 hours with the size of 0.1 mm×0.1 mm×0.05 mm. The product was confirmed by mass spectroscopy. A photograph of the crystals grown is shown in FIG. 1.

X-ray crystallography of the tetragonal plates showed a space group P422 and the following unit cell constants: a=b=91.071Å, c=37.665 Å, α=β=γ=120°.

Example 2

The same experiment was repeated as in Example 1 and mixed with a reservoir solution of 10% iso-propanol, 10% polyethylene glycol, 0.1M glycine buffer at pH=8.5.

Example 3

Batch Crystallization: rhPTH (SEQ ID NO: 1) at a concentration of 10 mg/ml was mixed with 50% iso-propanol, 100 mM Tris, pH=7.5, 0.2M sodium citrate at 1:1 ratio in the test tube. Crystals appeared within 48–96 hours with the size of 0.1 mm×0.1 mm×0.05 mm.

Example 4

Figure 2:
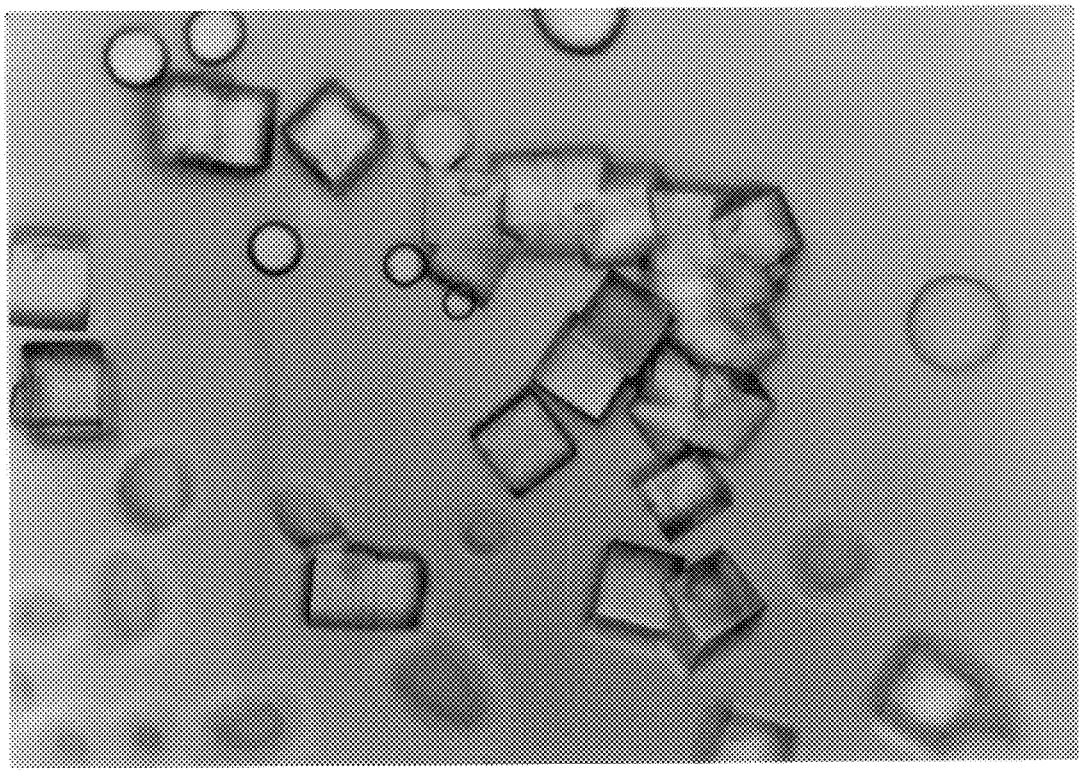
FIG. 2 is a photograph showing PTH(1–34) crystals grown from Example 4.

The protein was prepared in the same manner as in Example 1 and mixed in 1:1 ratio with reservoir solution (0.8M potassium phosphate, 0.8M sodium phosphate, pH=5.0). Cubic crystals appeared within 48 hours at room temperature with the size of 0.1 mm×0.1 mm×0.1 mm. A photograph of the crystals grown is shown in FIG. 2.

X-ray crystallography of the cubic crystals showed a space group P422 and the following unit cell constants: a=b=91.071Å, c=37.665 Å, $\alpha=\beta=\gamma 90°$.

Example 5

The protein was prepared the same way as Example 1 and mixed in 1:1 ratio with reservoir solution (0.8M sodium fornate, 0.1M sodium acetate buffer at pH=4.5). The same crystals appeared as in Example 4.

Example 6 rhPTH(1–34) (SEQ ID NO: 2) was prepared from material previously purified and lyophilized. The lyophilized protein was solubilized in 20% glycerol, at the concentration from 5 mg/ml to 20 mg/ml. The protein was mixed with reservoir solution (2.4M ammonium sulfate, 5% isopropanol, 0.2 sodium citrate buffer, pH=5.0) at 1:1 ratio on silicon coated glass cover slips. These cover slips were inverted and sealed over wells containing 1 ml of reservoir solution. Hexagonal crystals appeared within 12–24 hours with the size of 0.2 mm×0.2 mm×0.6 mm.

X-ray crystallography of the hexagonal crystals showed a space group P622 and the following unit cell constants: a=b=30.169Å, c=110.597Å, $\alpha=\beta=90°$, $\gamma=120°$.

---

I claim:

1. Crystalline parathyriod hormone selected from the group consisting of PTH(1–34), PTH(1–37), PTH(1–38), and PTH(1–41).

2. The crystalline hormone of claim 1, said hormone being human PTH(1–34).

3. The crystalline hormone of claim 2, in the form of tetragonal plates having a space group P422 and the following unit cell constants: a=b=91.071Å, c=37.665 Å, $\alpha=\beta=\gamma=90°$.

4. The crystalline hormone of claim 2 in cubic crystalline form having a space group P422 and the following unit cell constants: a=b=91.071Å, c=37.665 Å, $\alpha=\beta=\gamma=90°$.

5. The crystalline hormone of claim 2, in hexagonal crystalline form having a space group P622 and the following unit cell constants: a=b=30.169Å, c=110.597 Å, $\alpha=\beta=90°$, $\beta=120°$.

6. A vial or cartridge containing a crystalline parathyroid hormone fragment selected from the group consisting of PTH(1–34), PTH(1–37), PTH(1–38), and PTH(1–41).

* * * * *